United States Patent [19]

Antwiler

[11] Patent Number: 5,437,598

[45] Date of Patent: Aug. 1, 1995

[54] AUTOMATION OF PLASMA SEQUESTRATION

[75] Inventor: G. Delbert Antwiler, Lakewood, Colo.

[73] Assignee: COBE Laboratories, Inc., Lakewood, Colo.

[21] Appl. No.: 185,487

[22] Filed: Jan. 21, 1994

[51] Int. Cl.⁶ .......................... B04B 9/10; A61M 1/36
[52] U.S. Cl. .......................................... 494/1; 494/10; 604/6
[58] Field of Search .................... 422/72; 436/45, 177; 494/1, 10, 16, 18, 21; 604/6

[56] References Cited

U.S. PATENT DOCUMENTS

| | | | |
|---|---|---|---|
| 3,655,123 | 4/1972 | Judson | 494/10 |
| 4,146,172 | 3/1979 | Cullis | 494/18 |
| 4,151,844 | 5/1979 | Cullis et al. | |
| 4,464,167 | 8/1984 | Schoendorfer | 494/10 |
| 4,498,983 | 2/1985 | Bilstad et al. | 210/97 |
| 4,608,178 | 8/1986 | Johannson et al. | |
| 5,102,407 | 4/1992 | Carmen et al. | 604/410 |
| 5,154,716 | 10/1992 | Bauman et al. | 604/410 |
| 5,199,938 | 4/1993 | Kohlstette | 494/10 |
| 5,281,342 | 1/1994 | Biesel et al. | 494/1 |
| 5,348,533 | 9/1994 | Papillon et al. | 604/6 |

FOREIGN PATENT DOCUMENTS

WO88/05691  8/1988  WIPO.

OTHER PUBLICATIONS

T. Simon et al., "Storage and Transfusion of Platelets Collected by an Automated Two-Stage Apheresis Procedure", (1992) *Transfusion* 32:624–628.

C. F. Högman, "The Bottom and Top System: A New Technique for Blood Component Preparation and Storage", (1988), *Vox Sang* 55:211–217.

R. G. Strauss et al., "Comparison of autosurge versus surge protocols for discontinuous-flow centrifugation plateletapheresis", (1987), *Transfusion* 27:6 pp. 499–501.

J. P. AuBuchon et al. "Optimization of Parameters for Maximization of Plateletpheresis and Lymphocytapheresis Yields on the Haemonetics Model V50", (1986), *J. Clin. Apheresis* 3:103–108.

*Primary Examiner*—David A. Scherbel
*Assistant Examiner*—Terrence R. Till
*Attorney, Agent, or Firm*—Greenlee and Winner

[57] ABSTRACT

A plasma sequestration system having a volume control system is provided. When a calculated volume of whole blood has been processed, the system switches from a fill to an empty cycle. The termination point is calculated in advance, based on the desired composition of the collected plasma, thus improving process control and product uniformity. The system is automated or partially automated using an optical sensor or marker to monitor the volume of packed red blood cells. When the red cells reach the marker or sensor, a signal is sent to the control system which then calculates the required fill volume. Processing continues until the calculated fill volume is reached, at which time the system automatically stops the collection cycle. The system also provides for two speed operation of the centrifuge as a safeguard against foaming which may result in aerosol formation and blood trauma. Foaming is reduced by reducing centrifuge speed as the packed red blood cells approach the stationary deflector in the centrifuge bowl.

23 Claims, 8 Drawing Sheets

AUTOMATION OF PLASMA SEQUESTRATION

The present invention relates generally to systems and methods for processing whole blood. More particularly, the invention relates to an automated or semi-automated plasma sequestration system and to a method for separating whole blood into useful components.

BACKGROUND OF THE INVENTION

Some medical practitioners believe that separating platelet-rich plasma from a patient's whole blood immediately prior to surgery and then sequestering it until the surgery is over, thereby avoiding trauma to the platelets, has therapeutic benefits. Although the benefits are not well understood, some proponents of plasma sequestration believe that it minimizes the potential for platelet activation and/or the harmful effects associated therewith. Plasma sequestration may be particularly useful for cardiovascular procedures involving blood oxygenation by minimizing the potential for damage to platelets and clotting factors. In plasma sequestration, whole blood is processed by withdrawing it from the patient, separating the plasma from the whole blood by centrifugation, and collecting the plasma for later reinfusion. The patient thus receives a supply of autologous plasma, including platelets and clotting factors, following surgery. Some proponents of plasma sequestration also believe that this procedure helps to reduce blood loss following surgery and/or enhances the rate of wound healing by supplying a source of post-operative platelets.

In addition to these potential therapeutic benefits, plasma sequestration may also reduce or eliminate the need for homologous blood. Procedures which reduce the need for homologous blood products are currently of particular interest due to the growing concern over the possibility of disease transmission via transfusions of homologous blood products. The use of autologous blood products eliminates the risk of exposure to transfusion-transmitted disease and reduces the risk of febrile/allergic transfusion reactions. The use of autologous blood products also eliminates the need for compatibility testing.

Known methods of plasma sequestration generally comprise the following steps: (1) collecting and anticoagulating the patient's whole blood; (2) processing the blood to separate plasma and red blood cells; (3) returning the red blood cells immediately after processing; and (4) returning the plasma during or immediately following surgery. The blood collecting step can occur during surgery (intraoperative) or before surgery commences (perioperative). In the separation step, the blood is pumped into a spinning centrifuge bowl. Red blood cells, being the most dense of the components, are packed within the centrifuge bowl at the most radially outward location, whereas the plasma forms a layer more radially inward relative to the packed red cell layer. Although platelets can be found throughout the plasma and red cell layers, they tend to concentrate in a relatively thin, whitish layer, called the buffy coat, located at the interface between the plasma and red cell layers. The speed at which blood is pumped into the bowl, the centrifuge speed, the centrifuge bowl design, and the interference of red cells as platelets migrate through them all affect the separation of blood components.

Various automated and semi-automated blood processing systems have been designed to optimize blood component separation efficiency while minimizing operator involvement. Most of these systems are designed for blood component separation in general, not specifically for plasma sequestration. Many of these systems use an optical sensing device to partially or fully automate component separation. U.S. Pat. No. 4,151,844 (Cullis et al.), for example, discloses a centrifugation pheresis system comprising an optical sensing device monitoring the buffy coat outlet tubing. The optical sensing device monitors the composition or optical density of the buffy coat leaving the separation chamber; low density indicates dilution with plasma, high density indicates red cell contamination. When the density of the buffy coat increases or decreases beyond a predetermined range, defining a desired buffy coat composition, the control circuit adjusts the rates of withdrawal of the red blood cells and the plasma accordingly.

T. Simon et al. (1992) "Storage and Transfusion of Platelets Collected by an Automated Two-Stage Apheresis Procedure," Transfusion 32:624–628 discloses an automated plasmapheresis system wherein a detector monitors the optical characteristics of the plasma in the outlet tubing. The control circuit then adjusts the rate of plasma flow and the centrifuge speed to increase platelet concentration (higher optical density) with minimal red cell contamination. If red cell contamination exceeds predetermined levels, the system diverts that plasma back to the centrifuge for repeat processing. Blood processing continues until the desired weight of plasma is produced.

U.S. Pat. No. 4,608,178 (Johansson et al.) and C. F. Högman (1988) "The Bottom and Top System: A New Technique for Blood Component Preparation and Storage," Vox Sang 55:211–217, disclose a "top/bottom" bag in which the upper plasa and the lower red cell portions can be simultaneously withdrawn from the bag without removing the intermediate buffy coat layer. The "top/bottom" bag includes a sensor to monitor the position of the buffy coat layer while the plasma is withdrawn from the top of the bag and the red cells are withdrawn from the bottom.

Other automated and semi-automated pheresis systems which utilize optical sensing devices include U.S. Pat. No. 5,102,407 (Carmen et al.); U.S. Pat. No. 5,154,716 (Bauman et al.); U.S. Pat. No. 4,498,983 (Bilstad et al.); WO 88/05691 (Brown et al.); and Strauss et al. (1987) "Comparison of Autosurge versus Surge Protocols for Discontinuous-Flow Centrifugation Plateletpheresis," Transfusion 27:499–501. U.S. Pat. Nos. 5,102,407 and 5,154,716 disclose blood fractionation systems which can be semi-automated with sensors, located within the fluid outlet ports, to monitor and control the withdrawal of the separated constituents. U.S. Pat. No. 4,498,983 discloses an automated blood processing system comprising an optical sensor positioned within the separation chamber. The sensor monitors the level of packed red cells and, when the level of packed red cells within the chamber reaches a predetermined level, initiates reinfusion of the processed blood. WO 88/05691 discloses a pheresis system comprising an interface sensor for monitoring the location of the interface between the separated plasma and packed red blood cells during centrifugation. Strauss et al. (1987) discloses a plateletpheresis system using optical sensors which reportedly "monitor all aspects of the collection cycle and [which] automatically adjust the machine settings and the speed of plasma recirculation." AuBuchon et al. ("Optimization of Parameters for Maximization of Plateletpheresis and Lymphocytapheresis Yields on the Haemonetics Model V50" (1986) J. Clin. Apheresis 3:103–108) discloses an automated apheresis system wherein the volume offset setting is adjusted to compensate for the donor's hematocrit.

Blood processing systems which rely on features other than optical sensing devices for automation (or partial automation) include U.S. Pat. No. 4,417,884 (Schoendorfer et al.); U.S. Pat. No. 4,402,680 (Schoendorfer); U.S. Pat. No. 4,968,295 (Neumann); and WO 90/01970 (Ford). U.S. Pat. No. 4,417,884 discloses a centrifuge blood processing system under the control of a timing mechanism, wherein the timing mechanism depends on the speed and duration of the centrifugal force. U.S. Pat. No. 4,402,680 discloses a system for separating blood components using a valve means, such as a stopper ball, which seals the outlet port based upon the specific gravity difference between the blood components. U.S. Pat. No. 4,968,295 discloses a blood fractionation system in which the centrifuge speed responds to the input blood flow rate, thus maintaining constant volume ratios of whole blood and blood fractions.

WO 90/01970 discloses an automated plasmapheresis system wherein the collection and reinfusion cycles depend on the volumes of collected components. Specifically, the collection cycle terminates and the reinfusion cycle begins when a predetermined volume of packed cells has been stored in a reservoir. Once the red cell reservoir is emptied, the system alternates between the collection and reinfusion cycles until a predetermined volume of plasma has been collected, at which time the systems stops.

Although many of the existing automated blood processing systems purport to provide improved separation efficiency and product uniformity, none provide a means for customizing the process to produce a desired product composition. More specifically, none of these separation systems permit customized separation to produce a specific product composition while accommodating multiple system parameters. Most existing systems merely stop the process at some preselected point, for example, when the plasma in the centrifuge outlet tubing exceeds a predetermined optical density or turns a certain color. In fact, the latter method is the only means for assessing completion of the fill cycle in existing plasma sequestration systems, which currently are not automated. Monitoring the outlet tubing to determine when to stop the fill cycle, however, results in an uncertain end point and an inconsistent product. A need therefore exists for a blood processing system, and more particularly a plasma sequestration system, which permits customized separations and which automatically determines when to stop the fill cycle and start the empty cycle.

SUMMARY OF THE INVENTION

The present invention provides improved systems apparatus and methods for plasma sequestration from whole blood. The invention allows collection of a plasma product (collected plasma or plasma fraction) having a selected cumulative hematocrit or a selected percent platelet harvest (i.e., platelet content). The hematocrit or platelet content of the collected product plasma can be chosen, for example, to adapt the product to any desired therapeutic application. Plasma sequestration is performed in a centrifuge adapted for processing in sequential fill and empty cycles. During a fill cycle, whole blood is supplied to the centrifuge, plasma (containing platelets) is separated from the red blood cells in the rotating centrifuge, and the product plasma (containing platelets) exits the centrifuge to be collected. During an empty cycle, the centrifuge is stopped and the separated red blood cell pack remaining in the centrifuge is removed and collected, typically in a reinfusion bag for reinfusion into the patient. Since the red blood cell pack builds up in the centrifuge as a function of the volume of whole blood processed, the fill cycle is stopped to avoid undesired red blood cell spill into the collected product plasma. This invention provides improved automatic and semi-automatic means for controlling the termination of the fill cycle and initiation of the empty cycle. More specifically, this invention eliminates the uncertainty of prior art processes by automatically calculating the maximum fill volume, $V_f$, for a given whole blood source, necessary to achieve the desired collected plasma product composition. The calculation is made for individual whole blood samples and takes into account differences in source blood hematocrit without the need for independent measurement of source hematocrit.

The fill volume, $V_f$, needed to achieve the desired product is calculated based on an empirically determined relationship of $V_f$ to a marker volume, $V_m$. $V_m$ is the volume of whole blood of a given source that must be supplied to the centrifuge to generate a predetermined fixed volume of red blood cell pack in the centrifuge. $V_m$ is determined for each fill cycle by monitoring the progress of the inner edge of the red blood cell pack radially inward toward the centrifuge axis. $V_m$ is the whole blood volume that must be supplied to the centrifuge for the inner edge of the red cell pack to reach a predetermined fixed point on the centrifuge radius (indicating a predetermined volume of red cell pack). The relationship (i.e., mathematical equation) relating $V_m$ to $V_f$ is derived by a best fit of data generated in trial plasma sequestrations where $V_f$ is selected as the whole blood volume that must be supplied to the centrifuge to give the desired plasma product content, i.e., desired product hematocrit or platelet content. In a semi-automated embodiment, $V_m$ is determined when the system operator signals the system controller that the predetermined fixed volume of red blood cell pack has been accumulated in the centrifuge. In a preferred embodiment, a marker is incorporated on or above the top of the centrifuge bowl, which allows visual monitoring of the inward progress of the red blood cell pack. The system controller continuously monitors the volume of blood supplied to the centrifuge during the fill cycle. The operator signals the controller when the red blood cell pack edge reaches the marker. The system controller sets $V_m$ equal to the volume of blood that has been supplied up to the point the operator gave the signal. The system controller calculates $V_f$ and when the monitored blood volume supplied equals the calculated $V_f$ volume, the fill cycle is terminated.

In a fully automated embodiment, $V_m$ is determined when an appropriate sensing device, rather than the system operator, signals the system controller that the inner edge of the red blood cell pack has reached a predetermined set position along a radius of the centrifuge bowl. $V_f$ is then calculated based on $V_m$ as described above in the semi-automatic embodiment. In a preferred fully automated embodiment, an optical sensing device is positioned in the system to monitor the approach of the red cell pack inner edge to the predetermined radial location, for example, positioned as the red blood cell detector is conventionally positioned in commercially available blood salvaging systems.

Another aspect of the invention reduces the generation of foam as the red blood cell pack approaches the deflector of the centrifuge. Reducing the speed of the centrifuge at or before the point the red blood cell pack edge reaches the deflector has been found to reduce foaming. More specifically, under typical operating conditions with an initial centrifuge speed of 4400 rpm, reducing the centrifuge speed to 2400 rpm at about the point when the red blood cell pack edge reaches the deflector reduces foaming. Reduction in foaming prevent blood trauma caused by foaming and safeguards against aerosol formation which may occur if foam is entrained in the [collection tube] stator and reaches the [tubing seals] rotating seals between the rotating bowl and stator.

The exact nature of this invention as well as other features and advantages thereof will be readily apparent from consideration of the specification, including the drawing. Those of skill in the art will appreciate that the invention described herein is susceptible to many modifications and variations without departing from its scope as defined by the appended claims.

BRIEF DESCRIPTION OF THE DRAWING

The accompanying drawings illustrate preferred embodiments of the invention, wherein.

DETAILED DESCRIPTION

Figure 1:
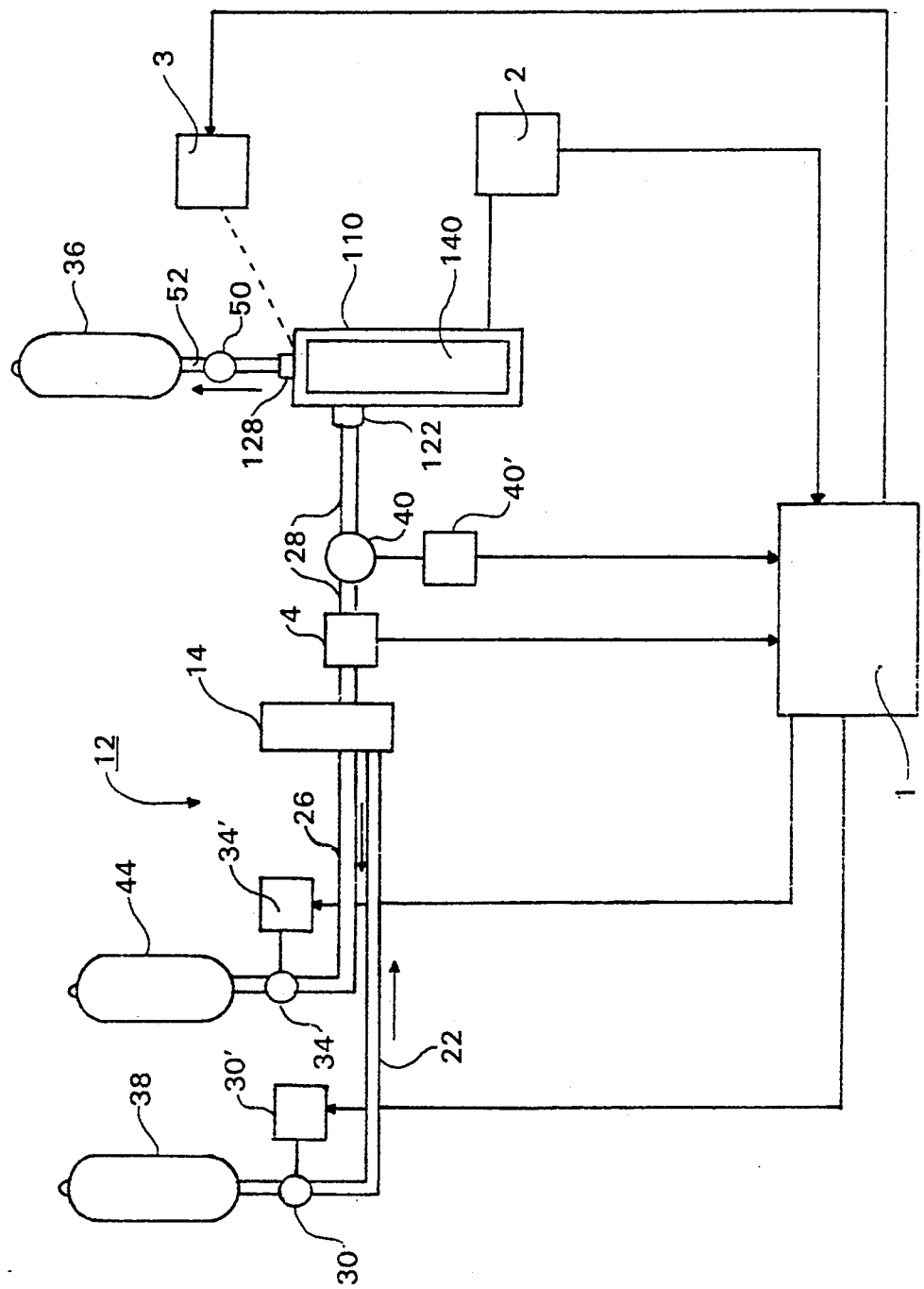
FIG. 1 is a general diagram of an automated plasma sequestration system in an embodiment of the present invention.

As used herein, the terms "collected plasma" and "product plasma" refer to plasma sequestration products separated by centrifugation from red blood cells. Product plasma contains plasma, typically as the major component platelets and other non-red blood cell components of whole blood. Product plasma typically also contains some level of red blood cells. Generally, it is desirable to maximize the platelet content of product plasma with a minimum of red blood cell contamination of plasma product. The present invention allows the collection of product plasma having a desired cumulative hematocrit or platelet content (which can be assessed as percent of platelets harvested). Product plasma hematocrit or platelet content can be chosen to adapt the product to any desired therapeutic application.

The inventive plasma sequestration system operates in sequential fill and empty cycles. Fill and empty cycles may be repeated in sequence until a desired amount of separated plasma is collected. A fill cycle may be subdivided into more than one plasma collection cycle, allowing collection of different plasma fractions. For example, plasma fractions having different platelet content can be separately collected within a single fill cycle. More specifically, platelet-poor and platelet-rich plasma fractions can be separately collected in a fill cycle.

During the fill cycle a red cell pack is formed in the centrifuge bowl. Because of their relatively high density, the red blood cell pack forms towards the radially outward portion of the centrifuge bowl. As whole blood is introduced into the centrifuge bowl, separated plasma exits near the center of the bowl for collection and the separated red blood cells remain in the centrifuge bowl. The volume of the red blood cell pack increases as the volume of whole blood passed into the system increases. A fill cycle is stopped before the red blood cell pack layer is thick enough (i.e., before the packed red blood cell volume is large enough) to allow significant undesired red blood cell spill over into the collected plasma.

The inventive system has improved control means for terminating the fill cycle and thereafter initiating the empty cycle, i.e. switching from the fill cycle to the empty cycle. This system control means actuates the switch over from fill to empty cycle when the volume of whole blood being supplied to the centrifuge equals a calculated fill volume, $V_f$. The system has a means for monitoring the volume of whole blood supplied to the centrifuge during the fill cycle and a means for determining the volume of whole blood, $V_m$, that was supplied to generate a predetermined fixed volume of red blood cell pack in the centrifuge. The system also has an automated means, e.g. a microprocessor, to calculate the fill volume, $V_f$, given $V_m$, based on an empirically predetermined equation relating $V_m$ to $V_f$. The empirical relation between $V_m$ and $V_f$ is determined in trial plasma sequestrations where $V_f$ is selected as the whole blood volume supplied that results in a separated plasma having a selected hematocrit or a selected platelet harvest.

The inventive system also has means for supplying a controlled flow of whole blood to the centrifuge and means for collecting the separated plasma and for removing and collecting separated red blood cells.

In a specific embodiment, the inventive system has a control means operatively associated with the means for removing and collecting red blood cells for terminating the empty cycle when red blood cells have been essentially removed from the centrifuge bowl. In a more specific embodiment, this control means employs a sensing device in the red blood cell discharge line which produces a signal upon detecting air in the discharge line indicative of an empty centrifuge bowl. The signal triggers the control means to terminate the empty cycle. Additionally, this signal can be employed to initiate a fill cycle if so desired.

In another specific embodiment, the inventive system has a means for controlling the rotational speed of the centrifuge. This speed controller can select between different speeds or completely stop rotation of the centrifuge. The control means is adapted to change the speed of rotation of the centrifuge when the whole blood volume supplied to the centrifuge equals a calculated speed-reduction volume, $V_s$. Reducing the rotation speed of the centrifuge at about the point when or before the red cell pack reaches the deflector of the centrifuge reduces foaming Preferably, the rotation speed of the centrifuge is reduced at the point when the red cell pack reaches the deflector. The speed-reduction volume is automatically calculated by the system controller based on $V_m$. The system is provided with a means for calculating $V_s$ using empirical predetermined equations relating $V_m$ to $V_s$ where $V_s$ is selected as the whole blood volume supplied to generate a red cell pack, the radially inward edge of which extends to a preselected point before that edge reaches the deflector. Preferable $V_s$ is selected as the volume needed to generate a red cell pack which extends to about the deflector.

In specific embodiments, the means for supplying a controlled flow of whole blood to the centrifuge, the means for removing and collecting separated red blood cells and the means for collecting the separated plasma comprise: a flexible tubing system including a supply line to introduce whole blood from a whole blood source to the centrifuge; a red blood cell discharge line from the centrifuge into a primary reinfusion bag; and a plasma discharge line from the centrifuge to a plasma collection bag. Each of these lines has a valve separating the line from the source or collection bag. These valves are automated. Both the supply line and the red blood cell discharge line have fluid pumps and the supply line also has a flow controller. The automated valves are employed in concert with the supply line pump to switch the system flows from the fill cycle to the empty cycle.

Referring now to the drawings, like numbers indicate like features and the same number appearing in more than one figure refers to the same element.

FIG. 1 shows schematically a plasma sequestration system of the present invention. A flexible tubing set as disclosed, as well as equipment in which to mount and use it, is produced by COBE Cardiovascular, a subsidiary of applicant's assignee, COBE Laboratories, Inc., under the trademark BRAT 2 TM. The tubing set 12 includes manifold 14, which communicates with blood collection reservoir line 22 and blood reinfusion bag line 26. The tubing set also includes a red blood cell reinfusion bag 44 connected to line 26 for collecting separated red blood cells removed from the centrifuge. Manifold 14 is connected by a centrifuge connecting line 28 with centrifuge inlet 22. Valves 30 and 34, for selectively opening and closing tubing 22 and 26, have associated therewith control means 30' and 34' for opening and closing valves 30 and 34, respectively. Control of valves 30 and 34 allows selection of the direction of flow of respective fluids. Valve means 30 and 34 are carried by the cooperating equipment referred to above, in which the tubing set is mounted in use. In an alternate embodiment (not shown), blood collection reservoir line 22 is connected directly to the patient using conventional blood extraction means.

Tubing set 12 also includes at least one plasma collection bag 36, which is supplied through outlet 128 of centrifuge bowl 140 and plasma collection line 52, and which is hung in use on the above-mentioned equipment; this equipment also rotatively drives bowl 140. Plasma collection valve 50 is a slide clamp, as is well known in the art.

The system further includes a reversible-direction peristaltic pump 40 which cooperates with line 28 to selectively pump in either direction therethrough. The reversible-direction peristaltic pump 40 has associated therewith a control/regulating means 40' for controlling the direction of flow and the flow rate of the blood and the separated red blood cells. The control/regulating means 40' also monitors the number of pump revolutions during a fill cycle and transmits this data to a microprocessor-based control system 1 for processing, the purpose of which is discussed below. In an alternate embodiment (not shown), an anticoagulant pump is also provided for pumping anticoagulant into the whole blood as the blood enters the tubing set through the blood collection reservoir line 22. Like the reversible-direction peristaltic pump 40, the anticoagulant pump has associated therewith a control/regulating means for adjusting the flow rate of the anticoagulant.

In FIG. 1 the centrifuge separator 110 is shown only schematically because the plasma sequestration system is operable with any centrifugal separator which is adapted for whole blood inflow and plasma outflow during centrifuge operation. For the automated plasma sequestration system exemplified in FIG. 1, the centrifuge separator 110 also has associated therewith a control/regulating means 2 for adjusting the speed of rotation of the centrifuge bowl and a photoelectric red blood cell detector 3, both described below.

To conduct plasma sequestration using the exemplified BRAT 2 TM system, blood is drawn from the patient, anticoagulated by conventional methods, and collected in a blood collection reservoir 38, a bag in the preferred embodiment. Alternatively, blood can be received directly from the patient and anticoagulated by methods known in the art. The anticoagulated whole blood is then drawn from the blood collection reservoir 38 (or, alternatively, directly from the patient) through valve 30, line 22, manifold 14, reversible-direction peristaltic pump 40, and line 28 into centrifuge bowl 140. Valve 30 and pump 40, together with their respective control means 30' and 40' and manifold 14, control the flow of blood into the centrifuge. Process fluid detector 4 detects air in the tubing line 28, to detect emptying of the centrifuge as discussed below.

Figure 2:
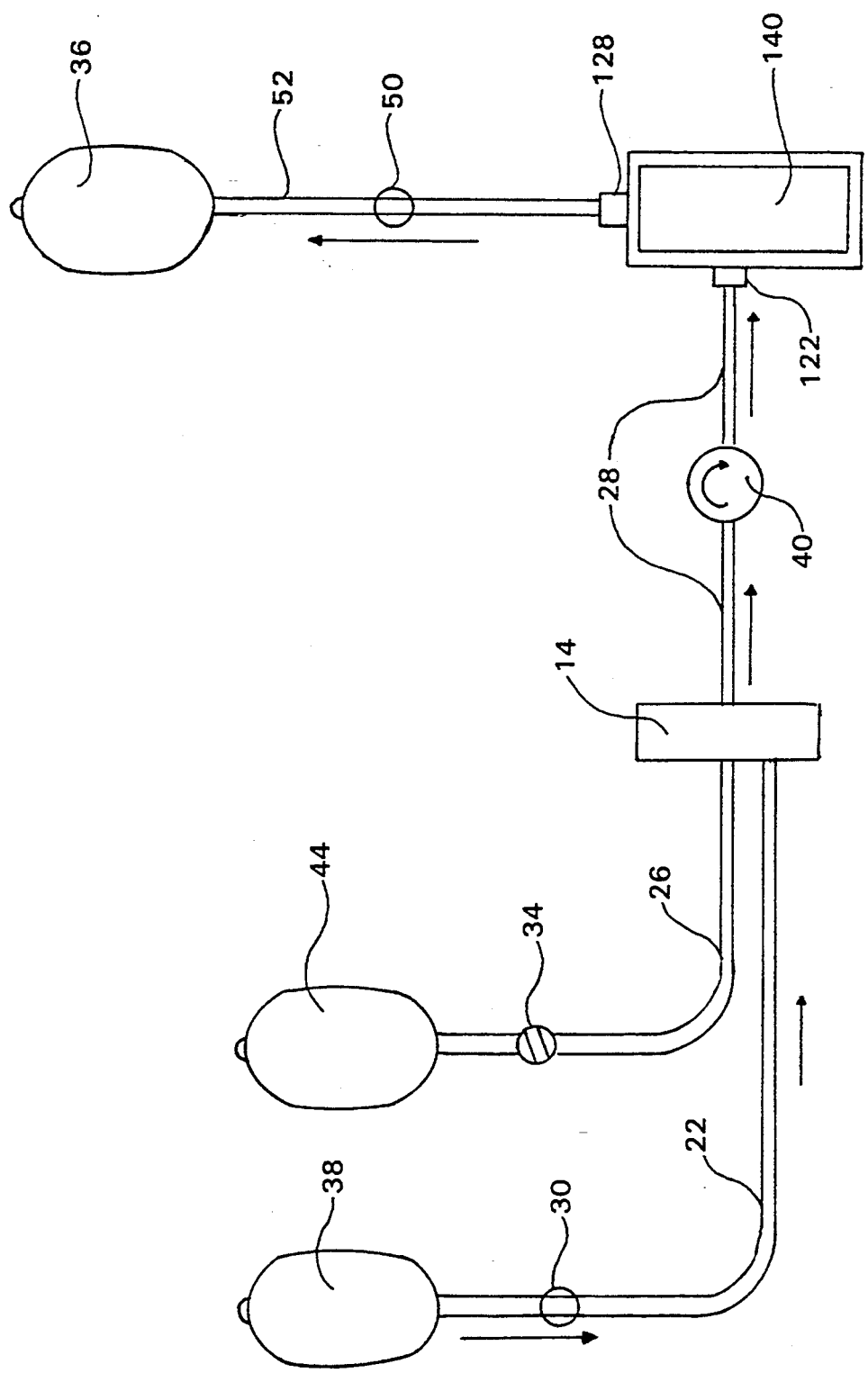
FIGS. 2 and 3 are schematic views of the flows in the plasma sequestration system during the fill and empty cycles, respectively.

During the fill cycle, as shown in FIG. 2, the anticoagulated whole blood enters the spinning centrifuge bowl 140 via centrifuge inlet 122. The blood collection reservoir valve 30 and plasma collection valve 50 are open; the reinfusion bag valve 34 is closed. In a preferred embodiment, the blood enters the centrifuge bowl 140 at a flow rate of about 100 mL/min, while the centrifuge bowl 140 spins at an initial rotational velocity of about 4400 rpm. The use of high centrifugal speeds during the initial fill cycle results in increased platelet concentration within the buffy coat layer, and thus improved platelet recovery. Such platelet concentration also facilitates the collection of plasma in two distinct fractions. The system can collect an initial platelet-poor fraction and a second platelet-rich fraction by separating the plasma fractions collected before and after a preselected point such as point (a) in FIG. 5, respectively.

During processing, red blood cells, being the most dense of the components, are packed within the centrifuge bowl 140 at the most radially outward location, the platelet-rich buffy coat concentrates inwardly adjacent to the red blood cells; the remaining plasma is relatively free of platelets and red blood cells. As processing continues, the platelet-poor plasma and, subsequently, the platelet-rich plasma exit the bowl during the fill cycle. Plasma continues to exit the centrifuge as whole blood is pumped in. After a calculated volume of whole blood, $V_s$, is supplied to the bowl, the reversible direction peristaltic pump 40 stops, the centrifuge slows to 2400 rpm, and the process pump starts again. $V_s$ is the amount of whole blood that must be supplied to the centrifuge to generate a red blood cell pack that extends to a preselected point approaching the deflector in the centrifuge. $V_s$ is not directly detected during operation, rather it is calculated based on $V_m$ which is determined during operation by visual or automated monitoring of the red blood cell pack. Processing continues at this reduced centrifugal speed until a calculated volume of blood, i.e., the fill volume ($V_f$, defined herein), has been processed. The system then automatically terminates the fill cycle and begins the empty cycle. Since the centrifuge bowl must fill with blood before plasma can exit and, thus, before the desired plasma composition is obtained, the fill volume ($V_f$) is necessarily greater than the volume of the bowl.

Figure 3:
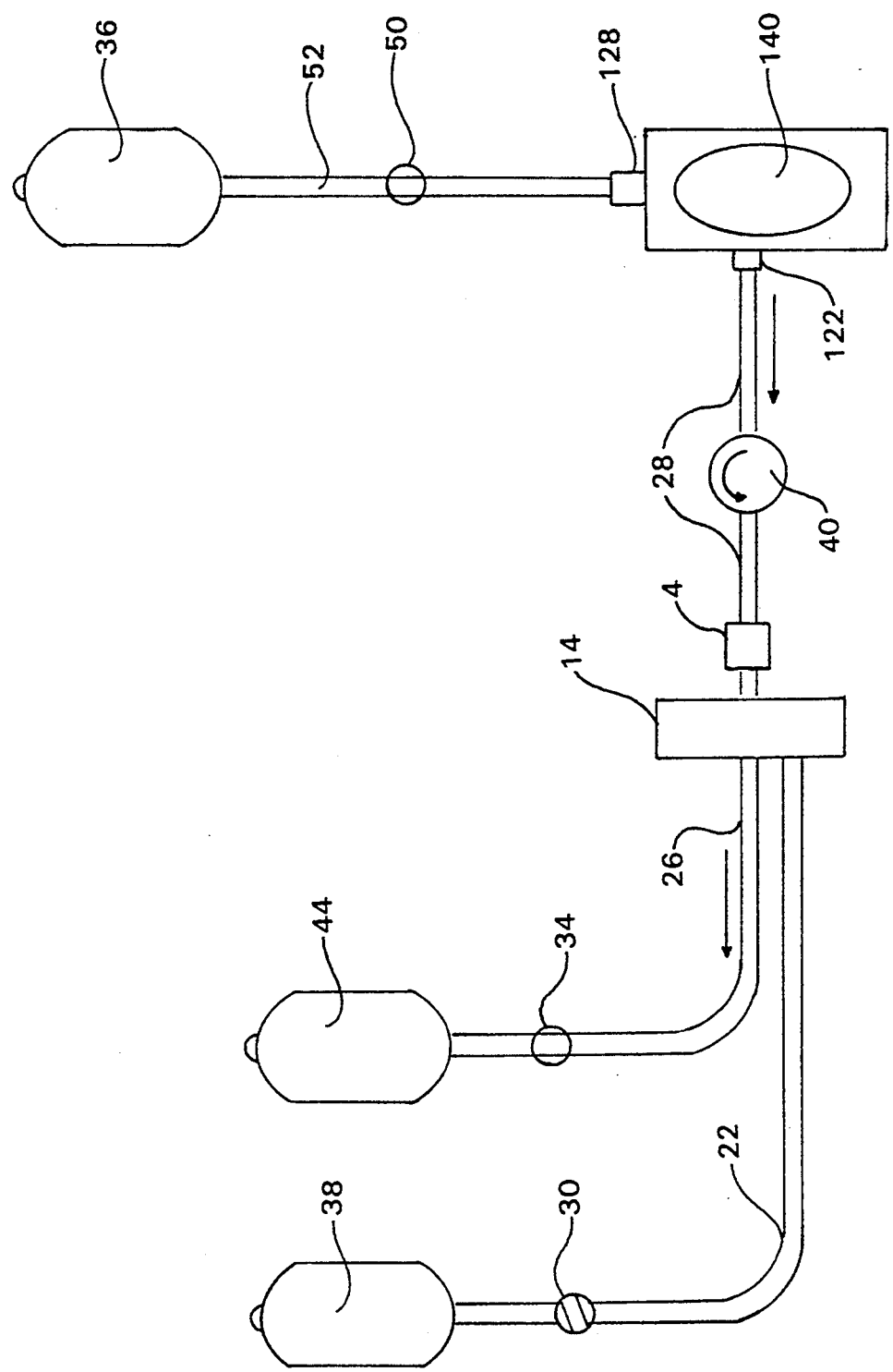

To initiate the empty cycle as shown in FIG. 3, the centrifuge bowl 140 stops spinning, blood collection reservoir valve 30 closes, and reinfusion bag valve 34 opens. The reversible-direction peristaltic pump 40 stops and then restarts in the opposite direction. During the empty cycle, the red blood cells in the centrifuge bowl 140 are pumped from the bowl via centrifuge inlet 122 through line 28, peristaltic pump 40, manifold 14, line 26 and valve 34 into the primary reinfusion bag 44. Valve 34 and pump 40, together with their respective control means 34' and 40' and manifold 14 (not shown), control the flow of red blood cells into the primary reinfusion bag 44. To avoid air embolism, the red blood cells from the primary reinfusion bag 44 are transferred to a secondary reinfusion bag (not shown) prior to reinfusion.

In a preferred embodiment, when the centrifuge bowl 140 is empty, a process fluid detector 4 detects air in the tubing line 28. When air is detected, the reversible-direction peristaltic pump 40 stops; the operator then decides whether to process another cycle.

Figure 4:
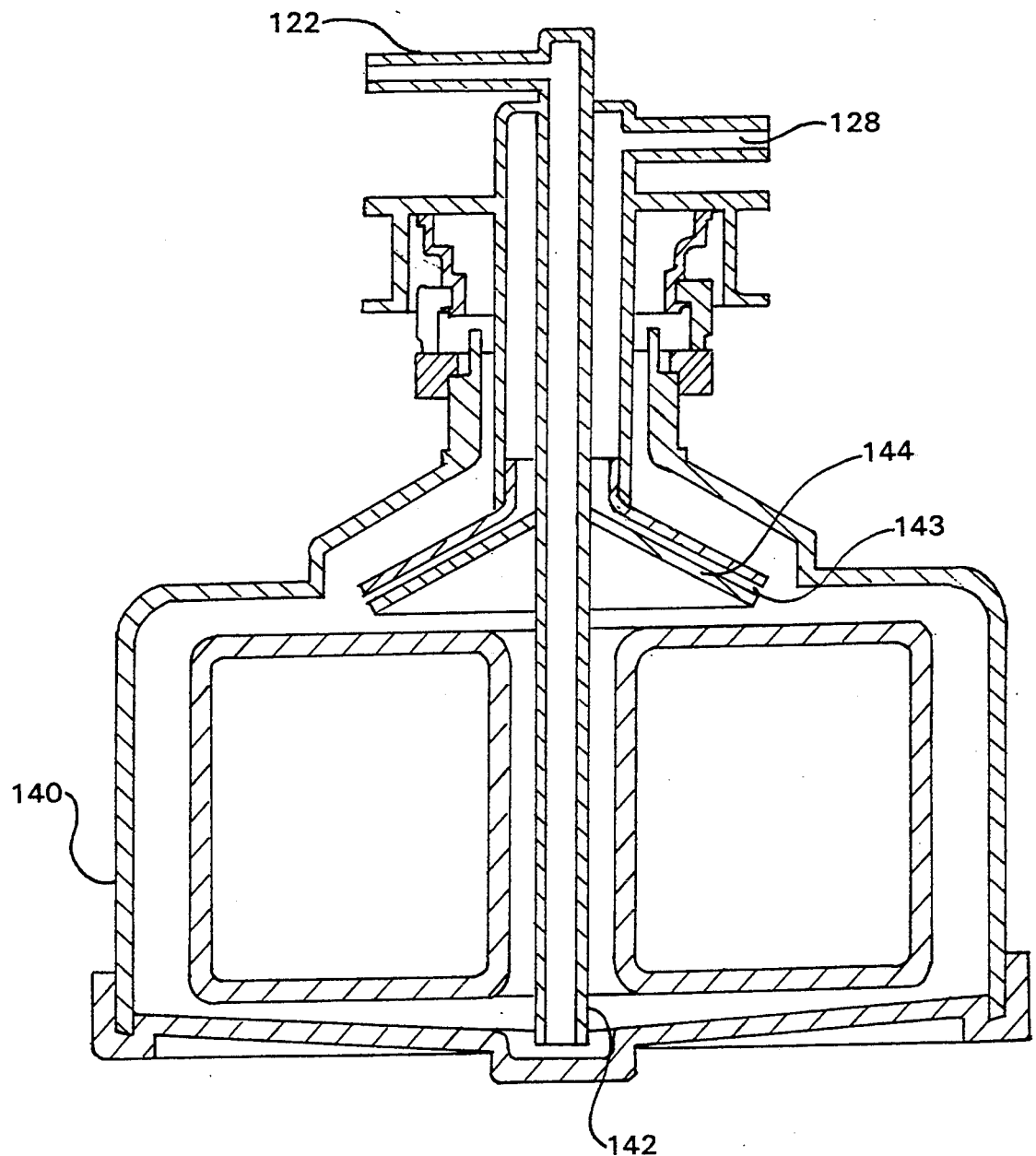
FIG. 4 is a side cross-sectional view of a centrifugal apparatus in a preferred embodiment of the invention.

FIG. 4 is a cross-sectional view of a centrifugal apparatus in a preferred embodiment of the invention. The anticoagulated whole blood enters the spinning centrifuge bowl 140 via centrifuge inlet 122. During the fill cycle, plasma exits the centrifuge bowl 140 through centrifuge outlet 128. The outer rotating bowl 140 comprises a stationary deflector 144 mounted to the bowl tube 142 to deflect the flow of plasma into the top channel 143. During the empty cycle, the red blood cells are pumped from the bowl 140 via centrifuge inlet 122. Centrifuge 110 can, for example, be of the type described in Feldman et al. (U.S. Pat. No. 4,684,361; issued Aug. 4, 1987), incorporated herein by reference.

Figure 5:
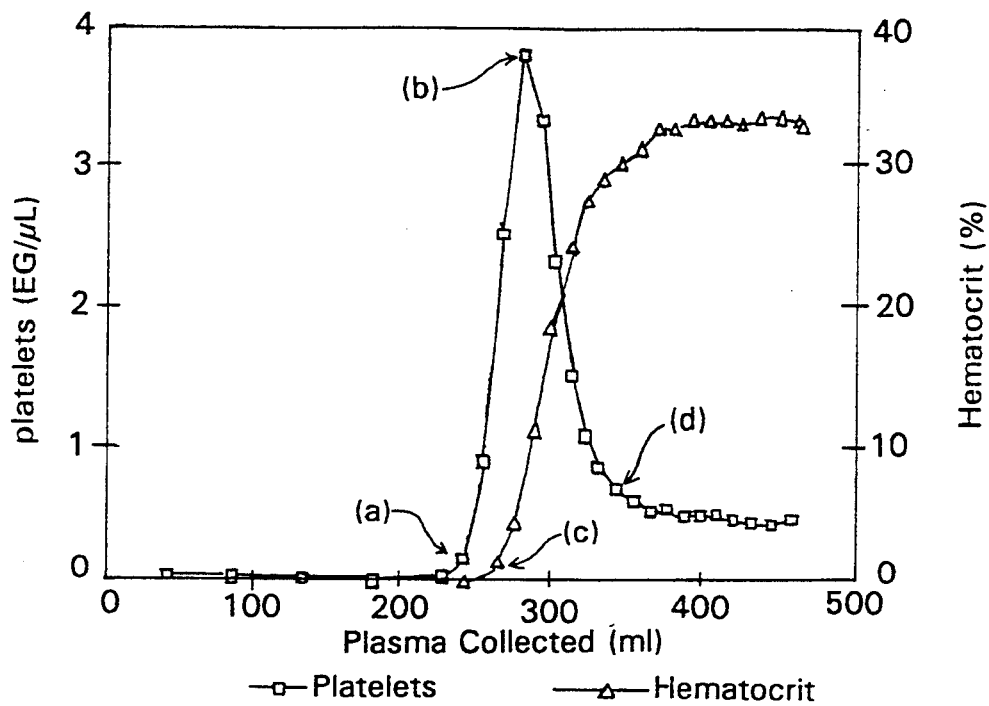
FIG. 5 shows an example of the relationship between the platelet count and the hematocrit as a function of the volume of plasma collected.

FIG. 5 shows an example of the relationship between platelets and red blood cells during plasma sequestration. The lines represent the platelet count and hematocrit of the separated plasma, plotted as a function of the collected plasma volume, as it passes through plasma collection line 52 into plasma collection bag 36 (FIG. 1). To illustrate the normal distribution of formed elements in the plasma, the fill cycle was allowed to continue beyond the normal stopping point for plasma sequestration. In most prior art systems, plasma leaving the centrifuge bowl is observed visually. In these systems, plasma sequestration ends when the plasma turns pink indicating that red blood cells are spilling and presumably indicating that the buffy coat has been collected.

As FIG. 5 illustrates, to collect a significant fraction of the available platelets, and thus produce a platelet-rich plasma, processing must continue beyond the platelet count peak, represented by point (b). Most prior art systems terminate the process beginning at some point of red cell contamination. Although some red cell spillage is necessary to maximize platelet recovery, continued collection beyond a certain point, e.g. point (d), results in modest platelet capture and an increased red cell contamination. As can be seen in FIG. 5, after the onset of the appearance of red blood cells, platelet and red cell concentrations change extremely rapidly. Thus, prior art processes which rely on operator observation and response suffer from uncertain end points and large product variation. Not only is the color change associated with the onset of red cell contamination subjective, but individual response times vary. These differences in color perception and response times can have significant effects on the platelet concentration and hematocrit of the resulting plasma product.

The instant invention resolves the problems associated with the prior art systems by instituting a volume control system. When a calculated volume of blood has been processed, the system switches from the fill to empty cycle. The system begins collecting plasma as soon as it is available and, importantly, stops collection at a calculated fill volume of whole blood supplied after the platelet peak has been reached. The particular stop point is selected depending on the desired composition of the collected plasma, e.g., the desired platelet concentration and hematocrit.

In one aspect of the invention, the microprocessor-based control system 1 (FIG. 1) determines the volume of blood to be processed, the fill volume ($V_f$), is a function of inlet hematocrit ($HCt_i$) according to the following equation:

$$V_f = f_1(HCt_i) \qquad (1)$$

wherein the inlet hematocrit ($HCt_i$) is measured experimentally by methods known in the art or is determined automatically by the control system using equation (3), defined below. In either case, the relationship between the required fill volume ($V_f$) and the inlet hematocrit ($HCt_i$) is an empirically defined function ($f_1$) dependent on system parameters such as the fill speed, the centrifuge speed, and the particular centrifuge bowl and tubing set used. In other words, $f_1$ is determined experimentally for the particular equipment and process conditions. In general, the system parameters which define $f_1$ can be held consistent, within manufacturing tolerances, from procedure to procedure.

As mentioned above, one of the significant advantages of the invention is improving product uniformity. According to this aspect of the invention, the system predicts the completion of the fill cycle using a volume control system based in part on the inlet hematocrit, as defined by equation (1). When the calculated volume of blood has been processed, the system automatically switches from the fill to empty cycle. Alternatively, the operator determines the end of the fill cycle at the outset of the procedure, again using equation (1). In either case, the red blood cells are transferred to a reinfusion bag and returned to the patient, while the plasma is collected for later infusion. The present invention eliminates the uncertainty of prior art processes by calculating when to switch from the fill to the empty cycle, thereby improving product uniformity.

As will be appreciated by those skilled in the art, equation (1), as well as equations (2) through (5) below, can be extrapolated to accommodate variations in one or more of the system parameters. For example, the system could be experimentally evaluated by varying both the inlet hematocrit and the processing pump speed. This would result in a set of equations that reflect variations in both inlet hematocrit and process pump flow rate. One can therefore customize the procedure to accommodate multiple system parameters, rather than just inlet hematocrit as exemplified herein.

Figure 7:
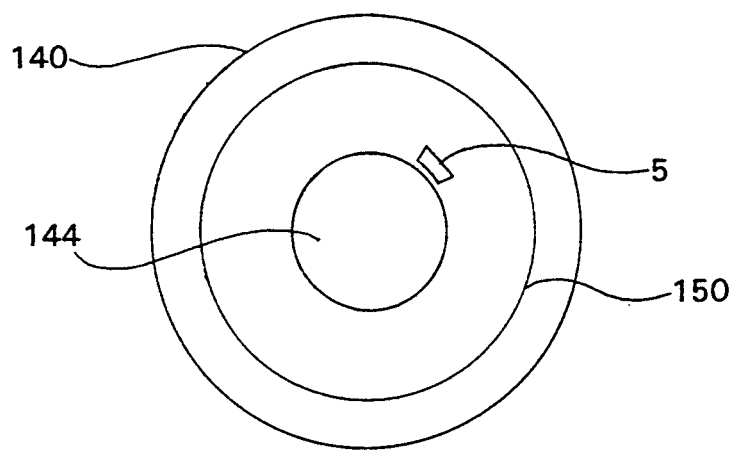
FIG. 7 is top cross-sectional view of a centrifugal apparatus for the system of FIG. 1.
Figure 6:
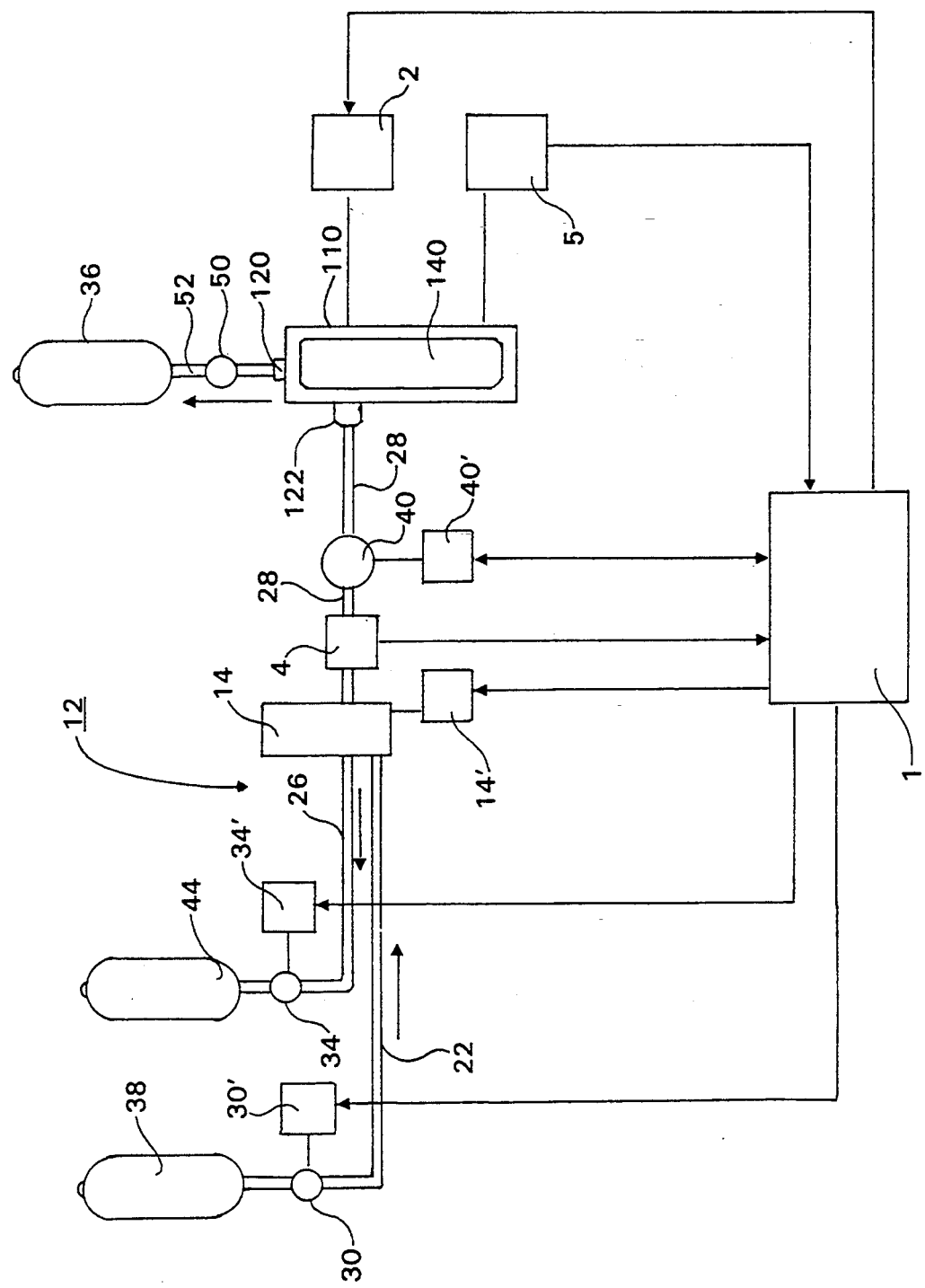
FIG. 6 is a general diagram of a semi-automated plasma sequestration system in an embodiment of the present invention.

In a "semi-automatic" embodiment, illustrated by FIG. 6, a red cell marker 5 is mounted in a fixed position within the centrifuge bowl 140. The "semi-automatic" embodiment resembles the plasma sequestration system shown schematically in FIG. 1, except that the red cell marker 5 funcitonally replaces red blood cell detector 3. The red cell marker-can be located at any convenient place on or above the centrifuge bowl 140 provided, however, that the location allows the operator to see the approach of the red blood cell pack to the marker. In a preferred semi-automatic embodiment, illustrated in FIG. 7 (a downward perspective view of the top of the centrifuge), red cell marker 5 is located above or on the top of the centrifuge bowl at a radial position from the centrifuge axis. The marker is positioned where, due to the volume displacement caused by the spacer or filler, increases in the red cell volume produce proportionately large increases in radial migration. In FIG. 7, the outer edge of the filler 150 in the centrifuge bowl is indicated. The marker is positioned radially between about the outer edge of filler 150 edge and about the outer edge of deflector 144. The operator uses the marker to determine $V_m$, the volume of whole blood required for the red cell pack to reach the marker. Both $V_m$ and $V_f$ are dependent on hematocrit of the whole blood being processed. The relationship between $V_m$ and the blood hematocrit ($HCt_i$) is a function ($f_2$) dependent on system parameters such as the fill speed, the centrifuge speed, and the particular centrifuge bowl and tubing set used. Thus, the volume to reach the marker ($V_m$) can be expressed as:

$$V_m = f_2(HCt_i) \text{ or} \quad (2)$$

$$HCt_i = g_2(V_m) \quad (3)$$

where $g_2$ is also a function of the system parameters. In view of equations (1) and (3), the relationship between $V_f$ and $V_m$ can be written as:

$$V_f = f_1[g_2(V_m)] \text{ or} \quad (4)$$

$$V_f = f_3(V_m) \quad (5)$$

where $F_3$ is another function of the system parameters. Thus, $V_f$ can be calculated from $V_m$ knowing $F_3$. This function, $f_3$, can be determined experimentally for the particular equipment and process conditions. In general, the system parameters which define $f_2$ and $f_3$ can be held consistent, within manufacturing tolerances, from procedure to procedure.

In accordance with this aspect of the invention, the operator signals the control system 1 when the advancing red cell pack reaches the marker (corresponding to blood Volume $V_m$). As previously mentioned, the control/regulating means 40' continuously tracks the number of pump revolutions per fill cycle and transmits this data to the control system. Once the operator signals the controller system, $V_m$ is set and the required fill volume ($V_f$) is calculated according to equation (5) above. Processing continues until the required fill volume ($V_f$) is reached, at which time the system automatically stops the fill cycle and begins the empty cycle.

The above-described "semi-automated" embodiment thus provides a significant advantage over the prior art systems by precisely and automatically calculating the end of the fill cycle based on actual experimental data. In this way, the "semi-automated" embodiment improves process precision, thus increasing product uniformity, by adjusting for minor variations in experimental conditions and equipment. Such experimental parameters include, for example, the small variations in bowl volumes common in manufactured bowls. The "semi-automatic" embodiment also combines the advantages of automation with the opportunity for operator intervention, thus enabling customized separation and finer process control.

Two-speed centrifuge separation can be provided in the semi-automated embodiment of the present invention as described below.

In a fully automated embodiment illustrated in FIG. 1, a red blood cell detector 3, rather than the operator, monitors the red blood cell pack and signals the control system 1 when the red blood cell pack reaches a predetermined radial position outward from the centrifuge axis, herein designated $P_m$. Preferably, $P_m$ is between the edge of the spacer 150 and the outer edge of the deflector 144 as in FIG. 7. The red blood cell detector 3 can be located at any convenient place outside of the centrifuge that allows detection of the point when the red blood cell pack intercepts $P_m$. For convenience and economy, for example, the detector 3 can be placed in the same location with respect to the centrifuge as in the conventional blood salvage application. For example, the red blood cell detector can be positioned as in the COBE BRAT TM blood salvaging system. This apparatus is commercially available and is described in the COBE BRAT TM system operator's manual published by COBE Laboratories (Lakewood Colo.), incorporated by reference herein in its entirety. The particular red blood cell detector used is not critical and can be any sensing device, for example, the red blood cell detectors typically used with blood salvage systems.

In accordance with this aspect of the invention, the optical sensing device 3 signals the control system when the advancing red blood cell layer reaches $P_m$. This point again determines $V_m$. As discussed above, the control/regulating means 40' tallies the number of pump revolutions per fill cycle and transmits this data to the control system. As with the "semi-automatic" embodiment, when the sensing device signals the control system, $V_m$ is set and $V_f$ is calculated using an experimentally derived equation relating $V_m$ and $V_f$. The equation is derived by best fit of data generated by trial plasma sequestrations which reflect actual experimental conditions and parameters, including the pump speed, tubing set, and location of the red cell detector. Processing continues until the required fill volume ($V_f$) is reached, at which time the system automatically stops the fill cycle and begins the empty cycle.

The presently preferred embodiment, illustrated in FIG. 1, thus provides the same advantages as the "semi-automated" embodiment, namely improved product uniformity, with the additional benefit of complete automation. The automated plasma sequestration system thus achieves improved product uniformity while minimizing operator involvement.

Both the fully automated and semi-automated embodiments of this invention can be run as a two speed separator. The plasma sequestration system in the exemplified BRAT-2 system as illustrated in FIG. 1 can comprise a control/regulating means 2 for adjusting the speed of rotation of the centrifuge bowl 140. The control/regulating means 2 reduces the centrifuge speed, preferably from about 4400 rpm to about 2400 rpm, when the packed red blood cells in the centrifuge bowl reach a predetermined point. Most preferably, the speed is reduced immediately before or at the point where red blood cells reach the deflectors.

According to this aspect of the invention, the microprocessor-based control system 1 calculates a speed-reduction volume ($V_s$), based on $V_m$. As with $V_f$ and $V_m$, $V_s$ and $V_m$ are related as:

$$V_s = f_4(V_m) \tag{6}$$

As described for $V_f$ and $V_m$ above, $f_4$ can also be empirically determined by a best fit to data generated in trial plasma sequestrations. Given $V_m$, the system controller calculates $V_s$ based on empirically-derived $f_4$ and when the volume of whole blood supplied to the centrifuge equals $V_s$, the controller slows the speed of the centrifuge.

Reducing the centrifuge speed, and thus the centrifugal force, when the packed red blood cells approach the deflectors in the centrifuge bowl reduces foaming. Although the speed can be reduced at any time during the fill cycle, the speed is preferably reduced immediately before or at the point when red blood cells reach the deflector 144. Thus, the empirically-derived equation relating $V_s$ to $V_m$ is preferably determined for $V_s$ selected as the volume of whole blood supplied to the centrifuge to generate a red blood cell pack that extends to about the outer edge of the deflector. Operating the sequestration initially at a high centrifuge speed can facilitate the collection of plasma in two fractions, an initial platelet-poor fraction followed by a second platelet-rich fraction.

In the semi-automated mode, marker 5 is preferably positioned such that its inside edge aligns as closely as possible with the outer edge of the deflector 144. With such positioning, $V_m$ is approximately equal to $V_s$ so that in a preferred semi-automatic embodiment, centrifuge speed reduction is triggered when the operator signals the system that the red blood cell pack has reached the inner edge of the marker (i.e., $V_m = V_s$). If the visual marker is placed significantly outward from the deflector, $V_s$ is calculated by the system controller using a predetermined equation relating $V_m$ to $V_s$ as described above for the fully automated mode. Once the operator signals the system, $V_m$ is set, $V_s$ is calculated. When the volume of whole blood supplied is $V_s$, the system controller reduces the speed of the centrifuge.

Figure 8:
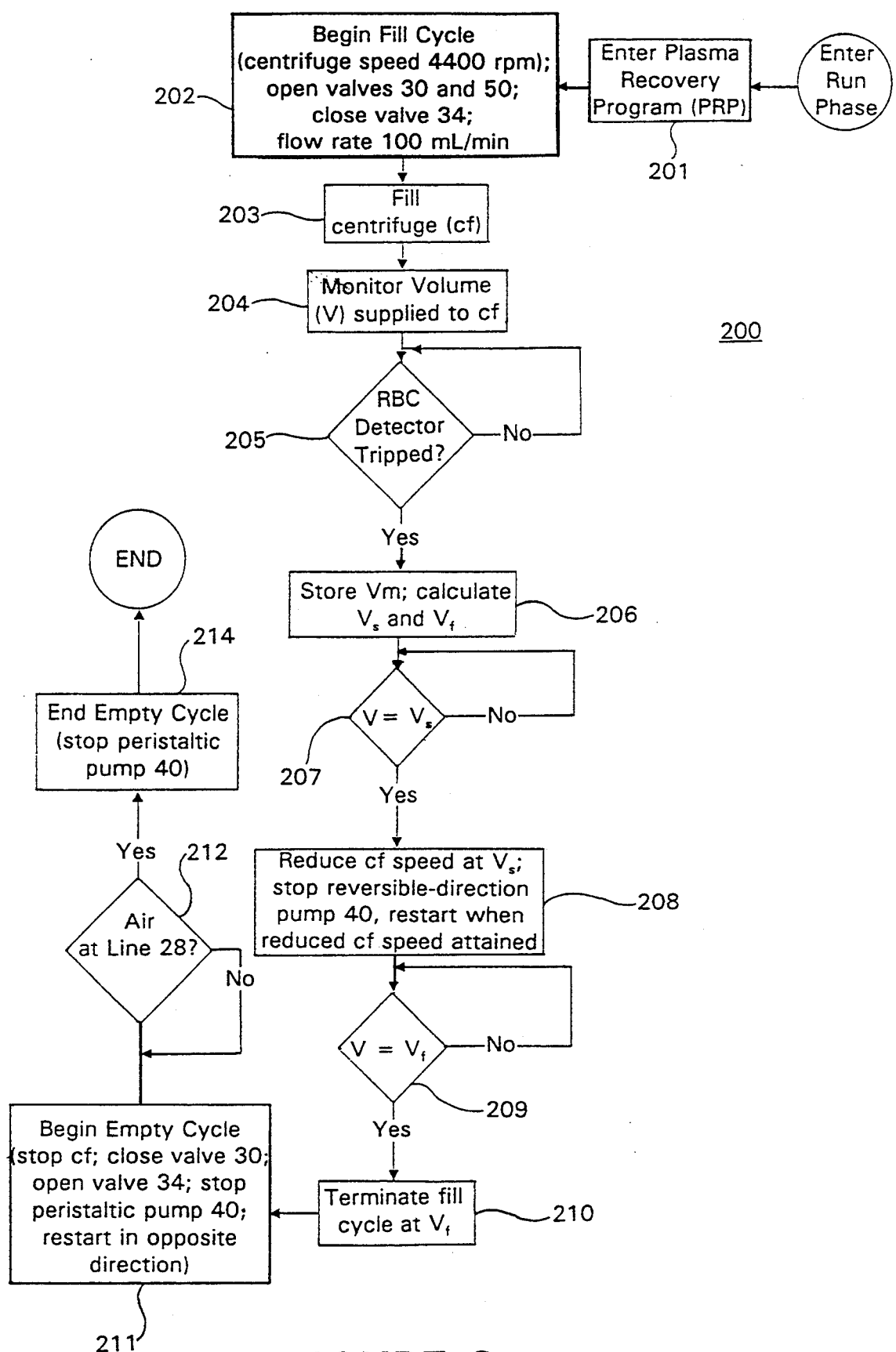
FIG. 8 is a flow chart of the control system used with the embodiment of FIG. 1.

FIG. 8 illustrates the control operation for the fully automated embodiment of FIG. 1 performed by the microprocessor-based control system 1 during the fill cycle. The control operation of FIG. 8 may be performed by any suitable control mechanism, but programmable control devices such as a microprocessor are advantageous for optimizing and customizing system performance.

Upon entering the plasma recovery program 200, the control system 1 at step 202 directs the establishment of fill cycle flows as illustrated in FIG. 2. The blood collection reservoir valve 30 is opened (plasma collection valve 50 is typically opened manually or may be automated); the reinfusion bag valve 34 is closed. In the exemplified BRAT-2 system, the reversible-direction peristaltic pump 40 is set to deliver a flow rate of about 100 mL/min of whole blood into the centrifuge; the centrifuge bowl 140 begins spinning at an initial speed of about 4400 rpm.

During the fill cycle, the reversible-direction peristaltic pump 40 continually monitors 204 the number of pump revolutions (a measure of volume supplied to the centrifuge) and transmits this information to the control system 1.

During the fill cycle, the control system 1 continually checks at step 205 for a signal from red cell detector 3, indicating that the red cell pack has reached a predetermined fixed point. The controller sets $V_m$ equal to the monitored blood supply volume at this point. The control system 1 then calculates the fill volume ($V_f$) and the speed-reduction volume ($V_s$) using predetermined empirical equations programmed into its microprocessor 206. The control system 1 then checks at 207 to determine whether the speed-reduction volume $V_s$ has been reached. If it has, control system 1 directs centrifuge speed control/regulating means 2 at step 208 to reduce the centrifuge speed, preferably to about 2400 rpm. Also at step 208, control system 1 directs reversible-direction peristaltic pump 40 to stop. When the centrifuge bowl 140 reaches 2400 rpm, pump 40 starts again.

Thereafter, the control system 1 checks at step 207 to determine whether the required fill volume ($V_f$) has been reached. If it has, control system 1 directs at steps 220 and 221 the establishment of empty cycle flows, as illustrated in FIG. 3. The centrifuge bowl 140 stops spinning, blood collection reservoir valve 30 closes, and reinfusion bag valve 34 opens. The reversible-direction peristaltic pump 40 stops and then restarts in the opposite direction.

In a preferred embodiment, during the empty cycle the control system 1 continually checks at step 212 for a signal from process fluid detector 4. When the signal arrives, indicating that air is present in tubing line 28 and the empty cycle is complete, the control system 1 directs entry at step 214 into a shut-down operation to halt the machine, unless the operator instructs the control system 1 to begin another fill cycle. If instructions are not received to begin another cycle, the control system 1 at step 214 directs reversible-direction peristaltic pump 40 to stop. Alternatively, the controller may be programmed to perform a set number of fill and empty cycles before shutting down.

The method for automating plasma sequestration of the invention is further detailed by reference to the following Examples. These Examples are provided for the purpose of illustrating the invention, and are not intended to be limiting thereof.

EXAMPLE I

PLASMA SEQUESTRATION USING BOVINE BLOOD

The fully automated plasma sequestration system, described above and illustrated in FIG. 1, was used to prepare plasma from bovine blood. The tubing set and machinery used was the autologous transfusion system produced by COBE Cardiovascular, a subsidiary of applicant's assignee, COBE Laboratories, Inc., under the trademark BRAT 2 ™. The red cell detector was the blood salvage detector used with the BRAT 2 ™, positioned in the same location as in the blood salvage application. The 250 mL Baylor bowl adapted for the BRAT 2 ™ and manufactured by COBE Cardiovascular, Inc. was used as the centrifuge bowl. The centrifuge speed during the initial fill was 4400 rpm; the reduced centrifuge speed was 2400 rpm. The pump fill speed was set to 100 mL/min.

In this case, the constants were experimentally chosen to yield a platelet harvest of approximately 70 percent and a hematocrit in the collected plasma of approximately 3 percent. The process parameters as defined by equations (1) through (6) were as follows:

$Hct_i = 87.1 - 0.182(V_m/mL) + 0.000131(V_m/mL)^2$ $V_f = -4.15 \text{ mL} + 1.506\ V_m$ $V_s = 22.7 \text{ mL} + 1.24\ V_m$

EXAMPLE 2

TRIAL PLASMA SEQUESTRATION USING HUMAN BLOOD

The fully automated plasma sequestration system, described above and illustrated in FIG. 1, was used to prepare plasma from fresh human blood. The tubing set and machinery used are described in Example 1. The 250 mL Baylor bowl adapted for the BRAT 2 ™ and manufactured by COBE Cardiovascular, Inc. was used as the centrifuge bowl. The centrifuge speed during the initial fill was 4400 rpm; the reduced centrifuge speed was 2400 rpm. The pump fill speed was set to 100 mL/min.

In this trial plasma sequestration, the inlet blood hematocrit was 44.8% and the inlet platelet count was 253.5 THSN/CU MM. The volume to fill the centrifuge bowl and tubing set to the plasma collection bag was 311 mL. $V_m = 339$ mL.

During the fill cycle, the harvested plasma was collected in a series of 10 to 50 ml test tubes. Each of the collected plasma samples were then measured for volume, hematocrit and platelet count. Individual and cumulative results are shown in Table 1. Platelet count was measured using commercially available Coulter Counter Model S-Plus IV, Coulter Electronics, Inc. Hialeah, Fla.

TABLE 1

| Tube # | Volume (mL) | Hematocrit (%) | Platelet Count E3/Micro L | Cumulative PRP Volume (mL) | Cumulative Hematocrit in PRP (%) | Cumulative Platelets Harvested (× E 6) | Cumulative Percent Platelets Harvested (%) |
| --- | --- | --- | --- | --- | --- | --- | --- |
| 1 | 47.0 | 0.1 | 35 | 47.0 | 0.10 | 1645 | 1.8 |
| 2 | 42.5 | 0.0 | 30 | 89.5 | 0.05 | 2920 | 2.9 |
| 3 | 26.0 | 0.0 | 62 | 115.5 | 0.04 | 4532 | 4.2 |
| 4 | 13.0 | 0.0 | 118 | 128.5 | 0.04 | 6066 | 5.4 |
| 5 | 11.0 | 0.1 | 285 | 139.5 | 0.04 | 9201 | 8.1 |
| 6 | 10.0 | 0.9 | 1072 | 149.5 | 0.10 | 19921 | 17.1 |
| 7 | 10.0 | 7.5 | 2253 | 159.5 | 0.56 | 42451 | 35.6 |
| 8 | 10.0 | 18.9 | 1929 | 169.5 | 1.64 | 61741 | 50.7 |
| 9 | 10.0 | 29.0 | 1388 | 179.6 | 3.17 | 75621 | 60.8 |
| 10 | 10.0 | 34.6 | 973 | 189.5 | 4.83 | 85351 | 67.3 |
| 11 | 8.0 | 36.9 | 654 | 197.5 | 6.13 | 90583 | 70.3 |

Figure 9:
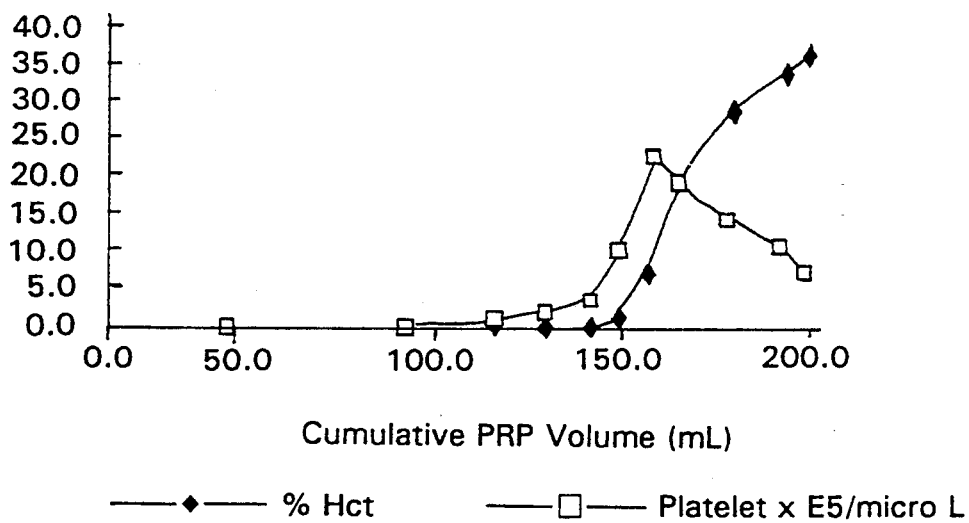
FIG. 9 is a graph of platelet count (open squares) and hematocrit (diamonds) in sequentially collected samples of separated plasma as described in Example 2 below. Data points represent measured platelet count and hematocrit in collection tubes 1-11 as listed in Table 1, below.
Figure 10:
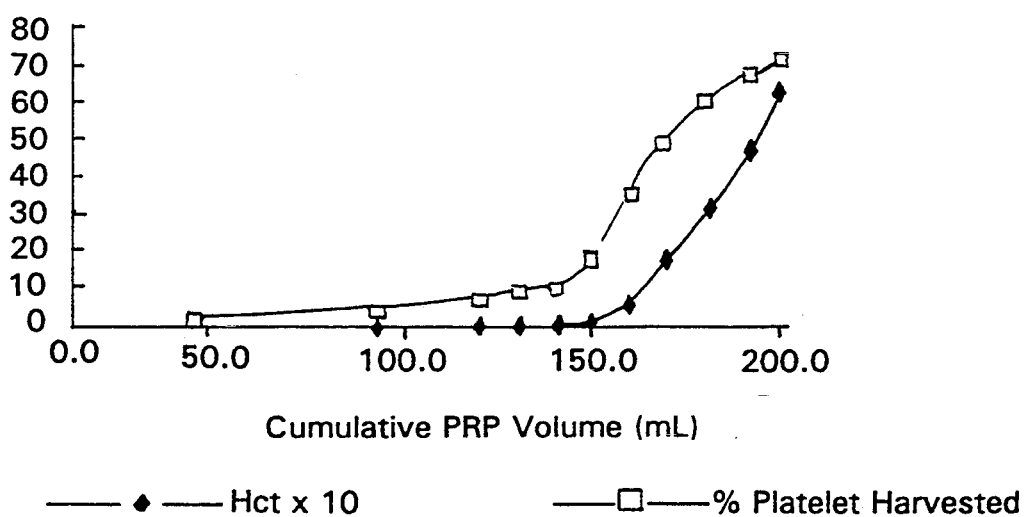
FIG. 10 is a graph of cumulative platelet count, as a percent of platelet harvested (open squares) and hematocrit (diamonds) in collected separated plasma as a function of collected plasma volume.

FIGS. 9 and 10 illustrate the distribution of platelets and red blood cells as a function of volume withdrawn through line 52, using the data in Table 1. Platelet count and hematocrit of the separated plasma are plotted as a function of the collected plasma volume. As is evident in FIG. 9, after the onset of the red blood cell spill, platelet and red blood cell concentrations change rapidly.

EXAMPLE 3

DERIVATION OF $V_m$ AND $V_f$ EQUATIONS

The fully automated and semi-automated plasma sequestration systems, described above and illustrated in FIGS. 1 and 6, were used to prepare plasma from fresh human blood. Plasma sequestration was conducted as described in Example 2. Data was generated from inlet blood ranging from 20% to 45% hematocrit.

The harvested plasma was collected in a series of 10 to 50 ml test tubes. Each of the collected plasma samples were then measured for volume, hematocrit and platelet count. Using this data, a model of the hematocrit and the platelet harvested in the platelet-rich plasma product was constructed as a function of the volume of PRP harvested or in terms of the fill volume ($V_f$), the blood volume at which to stop the fill cycle and start the empty cycle.

In this case, the constants were experimentally chosen to yield a platelet harvest of 70% or a hematocrit in the collected plasma product of 5% whichever occurred first. [In all cases, the 5% hematocrit occurred first.]

The plasma sequestration system employed was equipped with both a marker (5 in FIG. 7) and a red blood cell detector. The marker was radially positioned in the preferred position with its inner edge as close as possible to the outer edge of the deflector. In this configuration, the marker indicates $V_s$ as well as $V_m$ (semi-automatic mode). Thus, during these experiments, $V_m$ (automatic) is set when the red blood cell detector is triggered and $V_s$ can be determined by visually monitoring the marker. (Note that the point [$P_m$ herein] when the red blood cell detector is triggered is radially outward from the marker position.) In this configuration, experimental data could be collected to derive equations relating $V_f$ to $V_m$ (automatic) and $V_s$ to $V_m$ (automatic) for the automatic mode as well as $V_m$ (semi-automatic) for the semi-automatic mode of operation. (Note in the semi-automatic mode, the indicated marker position $V_s = V_m$.)

The fill volume at which the red cell detector tripped (R) and the fill volume to reach the marker $V_s$ and $V_m$ (semi-automatic mode) were recorded. In all cases, the centrifuge was slowed from 4400 rpm to 2400 rpm when the red cell pack reached the marker. First and second order linear regressions were fitted to the data meeting the above criteria. The second order fit resulted in only minimal increases in the correlation coefficient and significant reduction in the F-ratio. Therefore, the first order equations were chosen. They are as follows:

| First bowl: | automatic mode | $V_s = 1.4 + 1.230(V_m)$ |
| | automatic mode | $V_f = -96.3 + 1.743(V_m)$ |
| | semi-automatic | $V_f = -94.7 + 1.411(V_m)$ |
| Second bowl: | automatic mode | $V_s = -5.2 + 1.293(V_m)$ |
| | automatic mode | $V_f = -54.9 + 1.739(V_m)$ |
| | semi-automatic | $V_f = -47.1 + 1.343(V_m)$ | where all volumes are in mL. All correlation coefficients were greater than 0.997. As will be understood by those in the art, each of these equations could be expressed in terms of the inlet hematocrit.

EXAMPLE 4

PLASMA SEQUESTRATION USING HUMAN BLOOD

The fully automated and semi-automated plasma sequestration systems, described above and illustrated in FIGS. 1 and 6, respectively, were used to prepare plasma from fresh human blood. As described in Example 1, using the equations derived in Example 3, plasma sequestration was conducted on two different hematocrits: 28% and 38%. (Three batches of each sample were processed.) The target hematocrit in the collected plasma was 5% with a platelet harvest of 60-80%.

Each combination of inlet blood hematocrit (28% or 38%) and mode type (automatic or semi-automatic) was tested using three sets of disposables, for a total of twelve sets of disposables. For each disposable set, both first and second bowl data was collected.

Tables 2 and 3 show the average hematocrit and average percent platelets harvested for each mode and inlet hematocrit condition. The standard deviations are given in parentheses.

TABLE 2

| Average Hematocrit in Product Plasma | | |
| --- | --- | --- |
| | 28% Inlet Hct | 38% Inlet Hct |
| Automatic Mode | 5.8 (.6) | 5.7 (1.4) |
| Semi-automatic | 5.1 (.3) | 5.6 (.5) |

TABLE 3

| Average % Platelet Harvest in Product Plasma | | |
| --- | --- | --- |
| | 28% Inlet Hct | 38% Inlet Hct |
| Automatic Mode | 78.3 (4.4) | 66.5 (6.6) |
| Semi-automatic | 78.5 (2.7) | 59.2 (2.2) |

These results indicate that the empirically-derived equations of Example 3 are valid, i.e., calculate $V_f$ that will yield a product plasma with a defined hematocrit and platelet count.

From the foregoing, it will be appreciated that numerous variations and modifications may be effected without departing from the true spirit and scope of the novel concept of the invention. It is to be understood that the invention can be incorporated into other environments, and that no limitation with respect to the specific apparatus or blood source illustrated herein is intended or should be inferred. It is, of course, intended to cover by the appended claims all such modifications as fall within the scope of the claims.

I claim:

1. A system for plasma sequestration from red blood cells in whole blood in a centrifuge apparatus to produce a separated plasma having a desired cumulative hematocrit or a desired cumulative platelet harvest, said system having in sequence a fill cycle, during which whole blood is supplied to said centrifuge, said plasma is separated from said red blood cells such that a red cell pack is formed in said centrifuge and said separated plasma is collected, and an empty cycle, during which said separated blood cells remaining in said centrifuge are removed therefrom and collected, which comprises:

means for supplying a controlled flow of whole blood to said centrifuge;

means for monitoring the volume of whole blood supplied to said centrifuge;

means for collecting said separated plasma;

means for removing and collected said separated red blood cells;

means for determining the volume of whole blood, $V_m$, that was supplied to said centrifuge to generate a predetermined fixed volume of red blood cell pack in said centrifuge;

means for controlling the rotational speed of said centrifuge;

control means for terminating said fill cycle and thereafter initiating said empty cycle actuated when the monitored volume of whole blood being supplied to said centrifuge equals a calculated maximum fill volume, $V_f$;

automated means for calculating said maximum fill volume, $V_f$, operatively associated with said control means, said volume monitoring means and said means for determining $V_m$, which employs an empirically predetermined equation relating $V_m$ to $V_f$, where said equation is determined in trial plasma sequestrations where $V_f$ is selected as the centrifuge fill volume that results in separated plasma having a desired cumulative hematocrit or a desired platelet harvest.

2. The plasma sequestration system of claim 1 wherein said means for determining $V_m$ comprises a sensing device positioned above or on the bowl of said centrifuge for determining when the red cell pack volume reaches a predetermined fixed volume.

3. The plasma sequestration system of claim 2 wherein said sensing device is a photoelectric red blood cell detector.

4. The plasma sequestration system of claim 1 wherein said means for determining $V_m$ is a semi-automatic means in which a system operator visually determines when the red cell pack volume reaches a predetermined fixed volume as indicated by the red cell pack reaching a red cell marker on the centrifuge.

5. The plasma sequestration system of claim 1 wherein said predetermined equation is determined in trial plasma sequestrations where $V_f$ is selected as the centrifuge fill volume that results in separated plasma having a desired maximum cumulative hematocrit or a desired minimum platelet harvest.

6. The plasma sequestration system of claim 5 wherein said equations are determined such that $V_f$ results in a separated plasma having a maximum cumulative hematocrit of about 5%.

7. The plasma sequestration system of claim 5 wherein said equations are determined such that $V_f$ results in a separated plasma having a minimum cumulative platelet harvest of about 70%.

8. The plasma sequestration system of claim 1 in which said fill cycle comprises more than one plasma collection cycle for collection of plasma fractions having different platelet content which further comprises control means for sequentially terminating and initiating plasma collection cycles within said fill cycle.

9. The plasma sequestration system of claim 8 adapted for collecting a platelet-poor plasma fraction and a platelet-rich plasma fraction.

10. The plasma sequestration system of claim 1 wherein said means for calculating $V_f$ employs a microprocessor.

11. The plasma sequestration system of claim 1 wherein said predetermined equation is derived by a best fit of the equation to data collected in said trial plasma sequestrations.

12. The plasma sequestration system of claim 11 wherein said best fit is a first order linear regression.

13. The plasma sequestration system of claim 11 wherein said means for removing and collecting red blood cells from said centrifuge comprises a discharge line from said centrifuge to a primary reinfusion bag and a discharge line pump adapted for pumping said red blood cells from said centrifuge through said discharge line to said reinfusion bag and wherein said control means controls said discharge line pump and employs a sensing device in said discharge line for producing a signal upon detecting air in said discharge line indicative of an empty centrifuge apparatus.

14. The plasma sequestration system of claim 1 further comprising a control means operatively associated with said means for removing and collecting said red blood cells for terminating said empty cycle actuated when said red blood cells have been essentially removed from said centrifuge.

15. The plasma sequestration system of claim 1 further comprising control means for changing the speed of rotation of said centrifuge actuated when said monitored whole blood volume supplied to said centrifuge equals a calculated speed-reduction volume, $V_s$.

16. The plasma sequestration system of claim 15 wherein said centrifuge comprises a stator with a deflector and which further comprises automated means for calculating said speed-reduction volume, $V_s$, operatively associated with said centrifuge speed control means, said whole blood volume monitoring means and said means for determining $V_m$, which employs an empirically predetermined equation relating $V_m$ to $V_s$, where said equation is determined in trial plasma sequestrations where $V_s$ is selected to be a centrifuge fill volume less than that where foaming of the red blood cell pack occurs.

17. The plasma sequestration system of claim 16 wherein said means for calculating $V_s$ is a microprocessor.

18. The plasma sequestration system of claim 16 wherein said centrifuge comprises a stator with a deflector and said speed-reduction volume, $V_s$, is set to be less than the whole blood volume that must be supplied to said centrifuge to generate a volume of red blood cell pack that extends to the deflector in said centrifuge.

19. The plasma sequestration system of claim 16 wherein said speed-reduction volume, $V_s$, is set to be equal to $V_m$.

20. The plasma sequestration system of claim 15 wherein said predetermined equation relating $V_m$ to $V_s$ is derived by a best fit of the data collected in said trial plasma sequestrations.

21. The plasma sequestration system of claim 18 wherein said best fit is a first order linear regression.

22. The plasma sequestration system of claim 1 wherein
said means for supplying a controlled flow of whole blood to said centrifuge, said means for removing and collecting said separated red blood cells and said means for collecting said separated plasma comprise:
a flexible tubing system which includes a supply line to conduct whole blood to be separated from a whole blood source to the centrifuge apparatus having a valve on said supply line and between said source and said supply line, a red blood cell discharge line from said centrifuge into a primary reinfusion bag having a valve on said red blood cell discharge line and between said reinfusion bag and said line, a plasma discharge line from said centrifuge into a plasma collection bag having a valve on said plasma discharge line and between said collection bag and said plasma discharge line and control means for opening and closing each of said valves of said discharge lines, both of said supply line and said red blood cell discharge line being operatively coupled to a pump and said supply line also comprising a flow controller.

23. The plasma sequestration system of claim 22 wherein
said supply line comprises, in whole blood flow sequence, a whole blood source line, a centrifuge connection line connected through a manifold, and said red blood discharge line comprises said centrifuge connection line and a reinfusion line connected through said manifold, said supply line pump and said discharge line pump being a single reversible flow pump having a directional flow control means in said centrifuge connection line, wherein during said fill cycle whole blood flows through said blood source line through said manifold and said centrifuge connection line to said centrifuge and the flow direction of said pump is toward said centrifuge, while during said empty cycle separated red blood cells flow through said centrifuge connection line through said manifold and said reinfusion line to be collected and the flow direction of said pump is out of said centrifuge, said control means for terminating said fill cycle and initiating said empty cycle comprising said directional flow pump control means and said discharge line valve control means and said supply line valve control means and said centrifuge control means operationally associated with said means for calculating $V_f$ and said means for monitoring the volume of whole blood supplied to said centrifuge such that when said monitored volume equals the calculated $V_f$ said fill cycle is terminated and the empty cycle is initiated by the following sequential controller steps:

stopping said reversible pump, stopping the rotation of said centrifuge, closing said supply line valve while opening said discharge line valve, and reversing the flow direction of said reversible pump.

* * * * *